(12) United States Patent
Albeck et al.

(10) Patent No.: US 9,216,197 B2
(45) Date of Patent: Dec. 22, 2015

(54) TOPICAL FORMULATIONS OF TELLURIUM-CONTAINING COMPOUNDS

(75) Inventors: Michael Albeck, Ramat-Gan (IL); Benjamin Sredni, Kfar-Saba (IL); Doron Firedman, Karmei Yosef (IL)

(73) Assignee: BIOMAS LTD., Jerusalem (IL)

( * ) Notice: Subject to any disclaimer, the term of this patent is extended or adjusted under 35 U.S.C. 154(b) by 776 days.

(21) Appl. No.: 12/440,727

(22) PCT Filed: Sep. 10, 2007

(86) PCT No.: PCT/IB2007/004220
§ 371 (c)(1),
(2), (4) Date: Mar. 11, 2009

(87) PCT Pub. No.: WO2008/032227
PCT Pub. Date: Mar. 20, 2008

(65) Prior Publication Data
US 2010/0055055 A1 Mar. 4, 2010

Related U.S. Application Data

(60) Provisional application No. 60/843,402, filed on Sep. 11, 2006.

(51) Int. Cl.
*A61K 8/23* (2006.01)
*A61K 33/24* (2006.01)
*A61K 8/02* (2006.01)
*A61K 31/555* (2006.01)

(52) U.S. Cl.
CPC . *A61K 33/24* (2013.01); *A61K 8/02* (2013.01); *A61K 8/23* (2013.01); *A61K 31/555* (2013.01)

(58) Field of Classification Search
CPC .................................. A61K 8/02; A61K 8/23
See application file for complete search history.

(56) References Cited

U.S. PATENT DOCUMENTS

| | | | |
|---|---|---|---|
| 3,777,020 A * | 12/1973 | Johnson | 514/25 |
| 4,981,681 A * | 1/1991 | Tosti | 514/161 |
| 5,271,925 A | 12/1993 | Sredni et al. | |
| 6,472,381 B1 * | 10/2002 | Albeck et al. | 514/162 |
| 6,747,008 B1 | 6/2004 | Rodgers et al. | |
| 2004/0060315 A1 | 4/2004 | Dinnage | |
| 2005/0239894 A1 * | 10/2005 | Steiger | 514/567 |
| 2006/0127469 A1 | 6/2006 | Perricone | |

FOREIGN PATENT DOCUMENTS

| | | | |
|---|---|---|---|
| IL | WO2005069735 | | 8/2005 |
| IL | WO2006030437 | | 3/2006 |
| WO | WO-87/00427 | * | 1/1987 |
| WO | WO2005060341 | | 7/2005 |
| WO | WO-2005/069735 A2 | * | 8/2005 |

OTHER PUBLICATIONS

Sredni et al., Hair Growth Induction by the Tellurium immunomodulator AS101: Association with Delayed Terminal Differentiation of Follicular Keratinocytes and RAS-Dependent Up-Regulation of KGF Expression, Feb. 2004, FAESB Journal, vol. 18, pp. 400-402.*
International Search Report and the Written Opinion Dated Jul. 22, 2008 From the International Searching Authority Re.: Application No. PCT/IB07/04220.
Lima et al. "A Novel Organotellurium Compound (RT-01) as a New Antileishmanial Agent", Korean Journal of Parasitology, 47(3): 213-218, Sep. 2009.
Persike et al. "Protective Effect of the Organotelluroxetane RF-07 in Pilocarpine-Induced Status Epilepticus", Neurobiology of Disease, 31: 120-126, 2008.

* cited by examiner

*Primary Examiner* — Ali Soroush
(74) *Attorney, Agent, or Firm* — Browdy and Neimark, PLLC

(57) ABSTRACT

Novel formulations of tellurium-containing compounds, which are suitable for topical application, are disclosed. The formulations are characterized by high chemical and physical stability and are easy to handle and use.

42 Claims, 3 Drawing Sheets

A

B

TOPICAL FORMULATIONS OF TELLURIUM-CONTAINING COMPOUNDS

RELATED APPLICATIONS

This Application is a National Phase of PCT Patent Application No. PCT/IB2007/004220 having International filing date of Sep. 10, 2007, which claims the benefit of U.S. Provisional Patent Application No. 60/843,402 filed on Sep. 11, 2006. The contents of the above Applications are all incorporated herein by reference.

BACKGROUND OF THE INVENTION

1. Field of the Invention

The present invention relates to novel formulations of tellurium-containing compounds and particularly to tellurium-containing formulations that are designed for topical application. The novel formulations of tellurium-containing compounds of the present invention are characterized by chemical and physical stability, which is applicable when the tellurium-containing compounds are present therein in low, as well as in high, and very high concentrations.

2. Description of the Related Art

Various tellurium-containing compounds have been described in the art as having therapeutic activity. A particularly effective family of tellurium-containing compounds is taught, for example, in U.S. Pat. Nos. 4,752,614; 4,761,490; 4,764,461 and 4,929,739, whereby another effective family is taught, for example, in PCT International Patent Application No. PCT/IL2005/000989, which are all incorporated by reference as if fully set forth herein.

One of the most promising compounds described in these patents is ammonium trichloro(dioxyethylene-O,O')tellurate, which is also referred to herein and in the art as AS101. AS101, as a representative example of the family of tellurium-containing compounds discussed hereinabove, exhibits antiviral (*Nat. Immun. Cell Growth Regul.* 7(3):163-8, 1988, *AIDS Res Hum Retroviruses.* 8(5):613-23, 1992), and tumoricidal activity (*Nature* 330(6144): 173-6, 1987; *J. Clin. Oncol.* 13(9):2342-53, 1995; *J. Immunol.* 161(7):3536-42, 1998).

Another promising tellurium-containing compound is $[TeO_4(COCHH)_2]_2$, which is also referred to herein and in the art as SAS.

SAS and other ditellurium-containing compounds have been shown to act as effective inhibitors of caspase-1/interleukin-1β enzyme b (ICE) and their use in various additional therapeutic applications have also been described (see, for example, PCT/IL2005/000989 supra).

It has been suggested that AS101, SAS, and other tellurium-containing compounds, act as immunomodulators that stimulate the innate and acquired arm of the immune response. For example, it has been shown that AS101 is a potent activator of interferon (IFN) in mice (*J. Natl. Cancer Inst.* 88(18):1276-84, 1996) and in humans (*Nat. Immun. Cell Growth Regul.* 9(3):182-90, 1990; *Immunology* 70(4):473-7, 1990; *J. Natl. Cancer Inst.* 88(18):1276-84, 1996). It has also been demonstrated that AS101, as well as other tellurium-containing immunomodulators, induce the secretion of a spectrum of cytokines, such as IL-1α, IL-6 and TNF-α, and that macrophages are one main target for AS101 (*Exp. Hematol.* 23(13):1358-66, 1995). It was further found that AS101 inhibits IL-10 at the m-RNA level, and that this inhibition may cause an increase in IL-12 and IFN-γ (*Cell Immunol.* 176(2):180-5, 1997; *J. Natl. Cancer Inst* 88(18):1276-84, 1996).

Use of tellurium-containing compounds, such as AS101 and SAS, for treating conditions in which inhibition of ICE is beneficial has also been shown (see, for example, International Patent Application Nos. PCT/IL2005/000990 and PCT/IL2005/000989, supra). In another example, tellurium-containing compounds, in particular AS101, were shown to have a stimulating effect on bone marrow cells (U.S. Pat. No. 4,946,437).

Tellurium-containing compounds, in particular AS101, are further known to treat or prevent gastritis or peptic ulcer (U.S. Pat. No. 5,576,347), and to treat or prevent babesiosis, a tick-born disease (U.S. Pat. No. 5,610,179). AS101 has also been shown to have protective effects against lethal and sublethal effects of irradiation and chemotherapy (*Blood* 85: 1555, 1995; *J. Nat. Cancer Inst.* 88: 1276, 1996; *In. J. Cancer* 86: 281, 2000; *J. Immunol.* 156: 1101, 1996; *J. Immunol.* 145: 1507, 1990; *Cancer Res.* 51: 1499, 1991).

Additional examples of medical conditions that are treatable by AS101 and other tellurium-containing compounds are described, for example, in WO 2005/069735, U.S. Provisional Patent Application Nos. 60/716,924, 60/716,923, 60/610,660, in PCT International Application No. PCT/IL2005/000992, in WO 2005/060341, in U.S. patent application Ser. No. 11/226,375 and in U.S. Pat. Nos. 4,752,614, 4,761,490, 4,764,461 and 4,929,739 (supra).

Exemplary medical conditions that are known to be treatable by AS101 and other tellurium-containing compounds therefore include, for example, IL-1 mediated diseases, inflammatory diseases, autoimmune diseases, destructive bone disorders, proliferative disorders, infectious diseases, degenerative diseases, diseases associated with cell death, an excess dietary alcohol intake disease, retinal disorders, uveitis, inflammatory peritonitis, osteoarthritis, pancreatitis, asthma, adult respiratory distress syndrome, glomerulonephritis, rheumatoid arthritis, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, human papilloma virus related skin and mucosal membrane ailments, papilloma, condilloma, warts, alopecia and other conditions associated with hair loss, graft versus host disease, organ transplant rejection, organ apoptosis after burn injury, osteoporosis, leukemia's and related disorders, myelodysplastic syndrome, multiple myeloma-related bone disorders, acute myelogenous leukemia, chronic myelogenous leukemia, metastatic melanoma, basal cell carcinoma, actinic keratosis, UV skin damage, irradiation and chemotherapy-related effects, Kaposi's sarcoma, multiple myeloma, hemorrhagic shock, sepsis, septic shock, burns, Shigellosis, Alzheimer's disease, Huntington's disease, Kennedy's disease, prion diseases, cerebral ischemia, epilepsy, myocardial ischemia, acute and chronic heart diseases, myocardial infarction, congestive heart failure, atherosclerosis, coronary artery bypass graft, spinal muscular atrophy, amyotrophic lateral sclerosis, multiple sclerosis, HIV-related encephalitis, aging, neurological damage due to stroke, ulcerative colitis, peptic ulcer, traumatic brain injury, spinal cord injury, hepatitis-B, hepatitis-C, hepatitis-G, yellow fever, dengue fever, or Japanese encephalitis, various forms of liver disease, renal disease, polycystic kidney disease, *H. pylori*-associated gastric and duodenal ulcer disease, HIV infection, tuberculosis, immunotherapy for the treatment of various forms of cancer, babesiosis, organ failure, meningitis and complications associated with coronary artery bypass grafts.

AS101 is also characterized by low toxicity, with the $LD_{50}$ values in rats following intravenous and intramuscular administration of AS101 are 500-1000 folds higher than the immunologically effective dose. AS101 is therefore considered as an attractive therapeutically active agent.

Topical application of tellurium-containing compounds and pharmaceutical compositions thereof, has been found effective in the treatment of various skin-related diseases and disorders.

Thus, tellurium-containing compounds were found exceptionally effective in treating skin and mucosal membrane ailments, caused by human papilloma viruses (HPV) (see, for example WO 2005/069735, supra). HPV is a very common virus that causes abnormal cells or growth of tissue on the skin of the body, thus causing abnormal tissue changes on the feet, hands, vocal cords, mouth and genital (sex) organs.

Another topical use of tellurium-containing compounds is in the treatment or prevention of alopecia and other conditions associated with hair loss (see for example, U.S. Provisional Patent Application No. 60/610,660, supra, U.S. Pat. Nos. 6,552,089 and 5,262,149). In human clinical studies (*FASEB J* 18: 400-402, 2004), AS101 exhibited the ability to protect cancer patients from both bone marrow toxicity and alopecia induced by chemotherapy. AS101 has been found to induce hair growth in nude mice, normal mice, and in humans. In nude mice, AS101 has been shown to exert this effect when applied systemically, orally or topically.

Other skin conditions which may be treated by topical application of tellurium-containing compounds, include basal cell carcinoma (BCC), actinic keratosis (AK) (U.S. Provisional Patent Application No. 60/716,923, supra), damages caused by exposure to UV irradiation (U.S. Provisional Patent Application No. 60/716,924, supra), psoriasis (U.S. Pat. No. 6,472,381), atopic dermatitis (also known as eczema), Kaposi's sarcoma, scleroderma, burns, scarring (see U.S. Provisional Patent Application No. 60/610,660) and metastatic melanoma (Sun et al. "*Anticarcinoma activity of a novel drug, 3-ethyl-3'-methyl-thiatelluracarbocyanine iodide (Te), a tellurium-containing cyanine targeted at mitochondria*", Clinical Cancer Research, 1996, Vol. 2, Issue 8, 1335-1340).

As is widely recognized in the art, pharmaceutical compositions for topical application typically include a relatively large concentration of the applied active ingredient.

While studying the features required for a tellurium-containing compound to exhibit a therapeutic activity, it has been found that organic and inorganic tellurium-containing compounds that are derived from tellurium dioxide and hence have one or more tellurium dioxo moieties are highly potent as therapeutically active agents.

Such tellurium-containing compounds are known to exhibit an oxidative potential and, under certain conditions, may be considered unstable, both physically and chemically. When formulated into pharmaceutical compositions, and particularly for topical application, in which their concentration is relatively high, compounds containing tellurium dioxo moieties may be involved in oxidation and other reactions, which may lead, for example, to coloration of the pharmaceutical composition, degradation of various components therein, and/or incompatibility with certain packaging materials. A particular disadvantage of such tellurium dioxo-containing compounds is seen when compositions containing same are packaged, or come in other contact, with metallic substances. Metals such as aluminum are rapidly oxidized by these compounds. Therefore, to date, tellurium-containing pharmaceutical compositions, which are intended for topical application, often include relatively low concentrations of the active ingredient.

Additional limitations associated with formulating active tellurium-containing compounds into compositions for topical application results from the relatively poor solubility of compounds such as AS101 and SAS in aqueous or oleaginous carriers. While some topical formulations are based on oils and other hydrophobic carriers, formulations that are based on aqueous or amphiphilic carriers are beneficially characterized by usage convenience, being easily applied, non-greasy, and particularly washable.

Pharmaceutical compositions of tellurium-containing compounds and various carriers have been described, for example, in International Patent Application Nos. PCT/IL2005/000990 and PCT/IL2005/000989 and U.S. Pat. Nos. 4,752,614; 4,761,490, 4,764,461 and 4,929,739 (supra). Amongst the various carriers cited therein, carriers comprising polyethylene glycol (PEG) have been mentioned in passing. However, the applicability of PEG-based tellurium-containing formulations for topical uses, as well as the chemical and physical stability of such formulations, have never been established nor practiced heretofore.

In view of the exceptional therapeutic characteristics of tellurium-containing compounds which are derived from tellurium dioxide and hence have one or more tellurium dioxo moieties, described hereinabove, there is a widely recognized need for, and it would be highly advantageous to have, stable tellurium-containing formulations for topical application.

SUMMARY OF THE INVENTION

One aspect of the present invention provides a formulation for topical application comprising a tellurium-containing compound having at least one tellurium dioxo moiety and a pharmaceutically acceptable carrier, the carrier being selected such that:

the tellurium-containing compound, at a concentration of 10 weight percents, is soluble, dispersible and/or suspendable therein; and the formulation is chemically and physically stable upon storage at room temperature for at least 30 days.

Another aspect of the present invention provides a formulation for topical application comprising a tellurium-containing compound in an amount up to about 25 weight percent and having at least one tellurium dioxo moiety and a pharmaceutically acceptable carrier, said carrier being selected such that:

said tellurium-containing compound, at a concentration of 10 weight percents, is soluble, dispersible and/or suspendable therein; and the formulation is chemically and physically stable upon storage at room temperature for at least 30 days.

According to further features in the preferred embodiments of the invention described below, one or more carriers is selected such that the formulation is stable upon storage for at least 6 months at room temperature.

According to still further features in the described preferred embodiments the carrier is selected such that the formulation is stable upon storage at 40° C. for at least 30 days.

According to still further features in the described preferred embodiments the carrier is selected such that the formulation is stable upon storage at 40° C. for at least 60 days.

According to still further features in the described preferred embodiments the carrier is selected such that the formulation is stable upon storage at 40° C. for at least 90 days.

According to still further features in the described preferred embodiments the carrier is selected such that the formulation is stable upon cycling at a temperature that alternates 4 times from −10° C. to 40° C. every 48 hours.

According to still further features in the described preferred embodiments the carrier is selected such that the formulation is stable upon cycling at a temperature that alternates at least 3 times from about −10° C. to about 40° C. about every 48 hours.

According to still further features in the described preferred embodiments the carrier is selected such that the formulation is stable upon centrifugation at about 3,000 RPM for 10 minutes and then at 10,000 RPM for an additional 10 minutes.

Another aspect of the present invention provides a chemically and physically stable formulation for topical application comprising a tellurium-containing compound, having at least one tellurium dioxo moiety, in a concentration of at least 5 weight percents of the total weight of the formulation and a pharmaceutically acceptable carrier.

According to further features in the preferred embodiments of the invention described below, in any one of the formulations described herein the carrier comprises a glycol or an alcohol.

According to further features in the preferred embodiments of the invention described below, in any one of the formulations described herein the carrier comprises at least one C1-4 alkylene glycol.

According to still further features in the described preferred embodiments the at least one alkylene glycol comprises a polyethylene glycol.

According to still further features in the described preferred embodiments the polyethylene glycol has an average molecular weight that ranges from about 100 Da to about 10000 Da.

According to still further features in the described preferred embodiments the carrier comprises a mixture of polyethylene glycols selected so as to provide the formulation with a desired consistency (e.g., viscosity) applicable for topical formulation and/or to provide a formulation that is conveniently applied and/or absorbed.

According to still further features in the described preferred embodiments the carrier further comprises at least one ingredient selected from the group consisting of a stabilizer, a penetration enhancer, a humectant, a deodorant, an aroma modifier, an antiperspirant, a sun screening agent, a sunless tanning agent, a hair conditioning agent, a pH adjusting agent, a sun blocking agent, a chelating agent, a preservative, an emulsifier, an occlusive agent, an emollient, a thickener, a solubilizing agent, an anti-irritant, a colorant, a propellant and a surfactant.

According to still further features in the described preferred embodiments the additional ingredient is selected from the group consisting of propylene glycol and DMSO.

According to still further features in the described preferred embodiments the carrier further comprises at least one penetration enhancer.

According to still further features in the described preferred embodiments a concentration of the penetration enhancer ranges from about 1 weight percent to about 10 weight percents.

According to still further features in the described preferred embodiments the at least one penetration enhancer is selected from the group consisting of propylene glycol (PG), dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol monolaurate (PGML), PHOSAL®, glycerol monolaurate (GML), lecithin, 1-substituted azacycloheptan-2-ones, alcohols, vegetable oil, phosphatidylcholine concentrate (PC), and mixtures thereof.

According to still further features in the described preferred embodiments the carrier further comprises at least one surfactant.

According to still further features in the described preferred embodiments a concentration of the at least one surfactant ranges from about 1 weight percent to about 10 weight percents.

According to still further features in the described preferred embodiments the at least one surfactant is selected from the group consisting of non-ionic surfactant, anionic surfactant, cationic surfactant and amphiphilic surfactant.

According to still further features in the described preferred embodiments the surfactant is selected from the group consisting of Tweens (polyoxyethylene sorbitan monolaurate), tritons (octoxynol), tyloxapol, pluronics, Brijes (non-ionic polyoxyethylene surfactants), Spans (sorbitan mono-octadecenoate), poloxamers and emulphors.

According to still further features in the described preferred embodiments any of the formulations described herein further comprising an additional active agent.

According to still further features in the described preferred embodiments the additional active agent is selected from the group consisting of an antibiotic agent, an antimicrobial agent, an anti-acne agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, a chemotherapeutic agent, an antidepressant, an anti histamine, a vitamin, a hormone, a keratolytic agent and an antidandruff agent.

According to still further features in the described preferred embodiments a concentration of the tellurium-containing compound ranges from about 0.01 weight percent to about 50 weight percents.

According to still further features in the described preferred embodiments a concentration of the tellurium containing compound ranges from about 1 weight percent to about 20 weight percents.

According to still further features in the described preferred embodiments a concentration of the tellurium-containing compound ranges from about 10 weight percents to about 20 weight percents.

According to still further features in the described preferred embodiments the tellurium-containing compound is selected from the group consisting of tellurium dioxide ($TeO_2$), a complex of $TeO_2$, a compound having general Formula I:

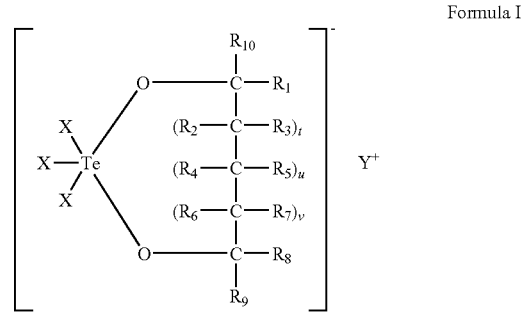

Formula I a compound having general Formula II:

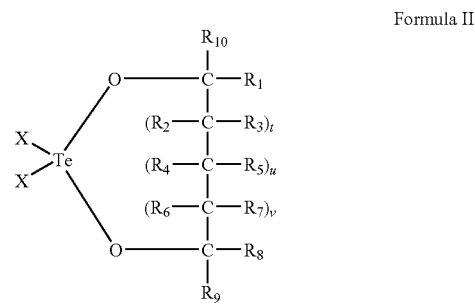

Formula II a compound having general Formula III:

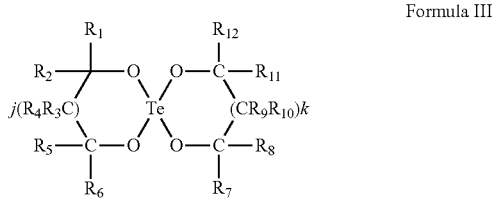

and
a compound having general Formula IV:

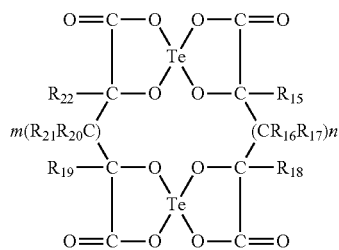

wherein:
each of t, u and v is independently 0 or 1;
each of m and n is independently an integer from 0 to 3;
each of j and k is independently an integer from 0 to 4;
Y is selected from the group consisting of ammonium, phosphonium, potassium, sodium and lithium;
X is a halogen atom; and
each of $R_1$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylaxnidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido.

According to still further features in the described preferred embodiments the tellurium-containing compound has general Formula I.

According to still further features in the described preferred embodiments t, u and v are each 0.

According to still further features in the described preferred embodiments $R_1$, $R_8$, $R_9$ and $R_{10}$ are each hydrogen.

According to still further features in the described preferred embodiments X is chloro.

According to still further features in the described preferred embodiments Y is ammonium.

According to still further features in the described preferred embodiments the formulation described herein is a hydrophilic formulation.

According to still further features in the described preferred embodiments the formulation described herein is a washable formulation.

According to still further features in the described preferred embodiments the formulation described herein has a viscosity in the range of from about 1,000 cpi to about 1,000,000 cpi at room temperature.

According to still further features in the described preferred embodiments the formulation described herein has a viscosity in the range of from about 3,000 cpi to about 30,000 cpi at room temperature.

According to still further features in the described preferred embodiments the formulation described herein is packaged in a packaging material and identified in print, in or on the packaging material, for use in the treatment of medical condition in which topical application of the tellurium-containing compound is beneficial.

According to still further features in the described preferred embodiments the formulation described herein is a the medical condition is selected from the group consisting of scleroderma, psoriasis, atopic dermatitis, scarring, a human papilloma virus related skin and/or mucosal membrane ailment, condilloma, warts, alopecia, hair loss, metastatic melanoma, basal cell carcinoma, actinic keratosis and UV skin damage.

According to still further features in the described preferred embodiments the formulation described herein is in a form selected from the group consisting of a cream, an ointment, a paste, a gel, a lotion, a milk, a suspension, a solution, an aerosol, a spray, a foam, a shampoo, a mousse, a serum, a swab, a pledget, a pad, a tincture, a patch and a soap.

According to an additional aspect of the present invention there is provided a method of treating or preventing a condition in which topical application of a tellurium-containing compound is beneficial, the method comprising administering to a subject in need thereof a therapeutically effective amount of a formulation as described herein.

According to a further aspect of the present invention there is provided a process of preparing the formulations described herein, the process comprising mixing the tellurium-containing compound and the carrier.

According to further features in preferred embodiments of the invention described below, the mixing is conducted at a temperature that ranges from about 10° C. to about 100° C.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of."

The phrase "consisting essentially of" means that the composition or method may include additional ingredients and/or steps, but only if the additional ingredients and/or steps do not materially alter the basic and novel characteristics of the claimed composition or method.

As used herein, the term "pharmaceutically acceptable" means approved by a regulatory agency of the Federal or a state government or listed in the U.S. Pharmacopeia or other generally recognized pharmacopeia for use in animals, and more particularly in humans. Herein, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "about" means+/−10%.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE PREFERRED EMBODIMENT

Figure 1:
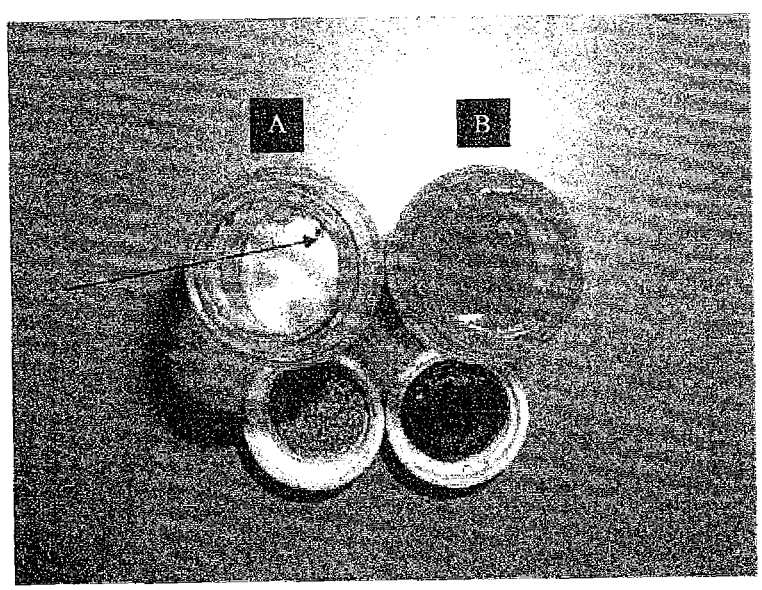
FIGS. 1A and 1B present photos of AS101 powder (FIG. 1A) and a 20% (by weight) solution of AS101 in DMSO (FIG. 1B), after storage for 30 days at ambient temperature in scintillation glass bottles having aluminum laminated non-sealed caps.

The present invention is of novel formulations of tellurium containing compounds. More specifically, the present invention is of tellurium-containing formulations that are designed for topical application. The novel formulations of tellurium-containing compounds of the present invention are characterized by chemical and physical stability when the tellurium-containing compound is present therein in low as well as in high and very high concentrations.

The principles and operation of the compositions and methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As mentioned in the Background section hereinabove, tellurium-containing compounds, for example, ammonium trichloro(dioxyethylene-O,O') tellurate (also known in the art as AS101) and $[TeO_4(COCH)_2]_2$ (also known in the art as SAS), have proven therapeutic properties. In one particular, topical application of tellurium-containing compounds and pharmaceutical compositions thereof, has been found effective in the treatment of various skin-related conditions, diseases and disorders, such as skin and mucosal membrane ailments caused by human papilloma viruses (HPV), in the treatment or prevention of alopecia and other conditions associated with hair loss, and in the treatment of basal cell carcinoma (BCC), actinic keratosis (AK), damages caused by exposure to UV irradiation, atopic dermatitis, Kaposi's sarcoma, scleroderma, burns, scarring and metastatic melanoma (see, for example, WO 2005/069735, U.S. Provisional Patent Application Nos. 60/610,660, 60/716,923 and 60/716,924, U.S. Pat. Nos. 6,552,089, 5,262,149 and 6,472,381, Sun et al. 1996, supra).

As is further discussed in the Background section hereinabove, tellurium-containing compounds, especially tellurium-containing compounds which are derived from tellurium dioxide and hence have at least one tellurium dioxo moiety, are known to exhibit an oxidative potential and, under certain conditions, may be considered unstable, both physically and chemically. Thus, when formulated into pharmaceutical compositions, particularly for topical application, in which their concentration is often relatively high, compounds containing tellurium dioxo moieties may be involved in oxidation and other reactions, which may lead, for example, to coloration of the pharmaceutical composition, and/or degradation of various components therein. As detailed in the Background section, when such tellurium dioxo-containing compounds are packaged, or come in other contact, with metallic substances, such as aluminum, the metals are rapidly oxidized by the tellurium-containing compounds.

The oxidative nature of tellurium-containing compounds is re-demonstrated in the Examples section below, wherein exemplary samples of AS101 (as a powder, as a 20% by weight solution in DMSO, and as an ointment containing the DMSO solution in combination with petroleum jelly) were visually tested. As can be seen in FIGS. 1A-B, the aluminum laminate cap of the bottles in which both the AS101 powder (FIG. 1A) and the 20% AS101 solution in DMSO (FIG. 1B) were stored, practically decomposed. Furthermore, a dark, black color was produced upon any contact of the tellurium-containing compound (AS101) with metal equipment, again confirming the oxidative nature thereof. The DMSO solution formulation and the ointment formulation further appeared to decompose upon storage.

Herein throughout, the phrases "tellurium dioxo moiety" and "tellurium dioxide moiety" are used interchangeably, and describe an —O—Te—O— group, in which the tellurium center can be further substituted.

Thus, presently available topical formulations comprising tellurium-containing compounds suffer from moderate stability, necessitating the use of special sealed containers during handling, packaging, storage and practice thereof. These special requirements invariably increase the cost of production of the pharmaceutical products based on tellurium-containing compounds, and lower the practicality of their use.

Figure 2:
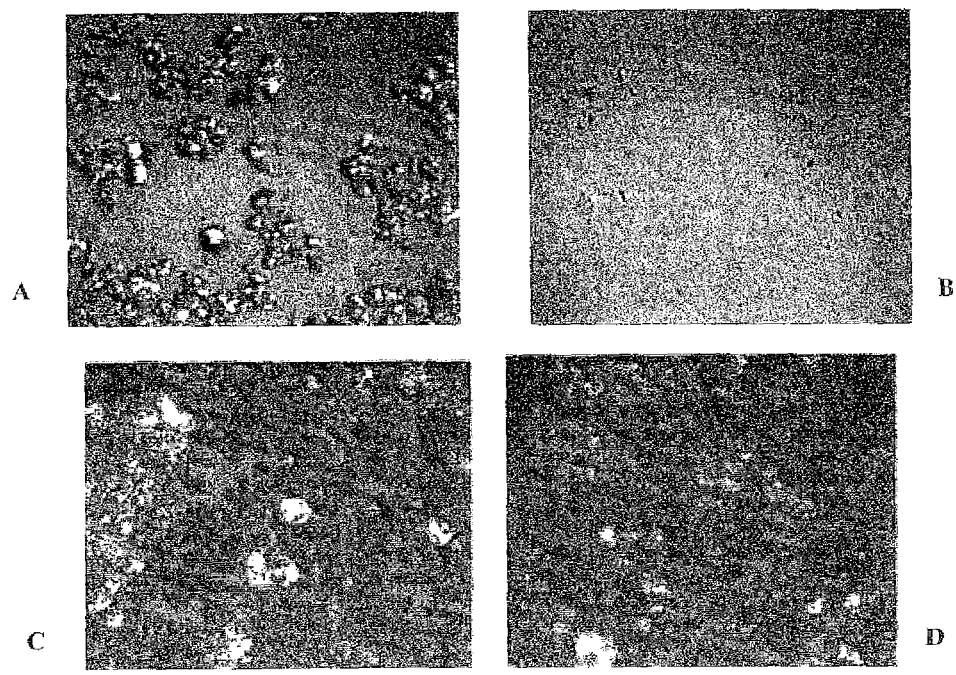
FIGS. 2A-2D present photos of AS101 powder (FIG. 2A), a 20% (by weight) solution of AS101 in DMSO (FIG. 2B) and AS101 ointment in DMSO/Petroleum jelly (FIGS. 2C and 2D) under polarized light.

As is further discussed in the Background section hereinabove, tellurium-containing compounds have a very low solubility in aqueous carriers, and thus most currently-available formulations are based on hydrophobic carriers (for example petrolatum, such as petroleum jelly cream) which, by often being greasy and staining, are less desirable. As demonstrated in the Examples section below, an exemplary tellurium-containing compound (AS101) was, on one hand, solubilized (FIG. 2B) yet moderately stable (FIG. 1B) in DMSO, and on the other hand, was not solubilized in the DMSO/petroleum jelly ointment, re-crystallizing into another polymorphic type (FIGS. 2C and 2D).

Novel, stable aqueous formulations comprising tellurium-containing compounds, which would be suitable for topical application are therefore highly desirable.

In a search of such novel formulations, it was surprisingly found that tellurium-containing compounds can be formulated into stable aqueous topical formulations, which are devoid of the disadvantages associated with the presently known tellurium-containing topical formulations described hereinabove.

As shown in the Examples section below, an exemplary topical formulation containing 12% of the tellurium-containing compound AS101 has been developed as a prototype formulation of substantially solubilized tellurium-containing compound. The formulation further comprised pharmaceutical inactive ingredients which are approved for topical prescription drugs by the FDA and the European authorities. The obtained product was a semi-solid hydrophilic ointment, characterized by a good skin feeling, ease of application, and a non-greasy, non-sticky nature. This formulation successfully passed a set of accelerated instability physical tests and further showed good chemical stability. Another exemplary topical formulation, containing 15% of the tellurium-containing compound AS101 has been developed and was also found to remain stable upon storage. Other exemplary formulations containing 12% of the tellurium-containing compound AS101 are also presented.

The present invention therefore successfully addresses the shortcomings of the presently known configurations by providing chemically and physically stable formulations of therapeutically active tellurium-containing compounds, suitable for topical application, allowing the formulation of stable tellurium-containing compounds in any desired concentration.

Thus, according to one aspect of the invention, there is provided a formulation for topical application which comprises a tellurium-containing compound, preferably a compound derived from tellurium dioxide which has one or more tellurium dioxo moieties. The formulation, according to this aspect of the present invention, further comprises a pharmaceutically acceptable carrier which is selected such that when the tellurium-containing compound is present therein in a concentration of 10 weight percents, it is soluble, dispersible and/or suspendable therein; and the formulation is chemically and physically stable upon storage at room temperature for at least 30 days.

Hereinafter, the phrase "pharmaceutically acceptable carrier" refers to a carrier or a diluent that does not cause significant irritation to the subject and does not abrogate the biological activity and properties of the administered compound. As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Hereinafter, the phrase "topical application" refers to direct application to an external surface or to a cavity of tissues of the body.

Topical application of the tellurium-containing compounds described herein is preferably effected by applying a therapeutically effective amount of a tellurium-containing compound onto a treated skin or mucosal area.

The treated area can be, for example, an area of the face, ears, neck, scalp, shoulder, back, forearm, hand, chest leg or vagina.

Herein, the phrase "treated area" encompasses the affected area as well as the tissues surrounding the affected area. The topical application is effected over and around the clinical manifestation.

The term "therapeutically effective amount" or "pharmaceutically effective amount" denotes that dose of an active ingredient or a composition comprising the active ingredient that will provide the therapeutic effect for which the active ingredient is indicated. Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated. Determination of a therapeutically effective amount is well within the capability of those skilled in the art.

The therapeutically effective amount or dose can be estimated initially from in vitro assays, e.g., performed on human or animal skin. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures experimental animals or humans. The data obtained from these in vitro and cell culture assays and animal or human studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

As demonstrated in the Examples section below, by selecting a suitable carrier, the tellurium-containing formulation can be obtained as a chemically and physically stable formulation, such that an exemplary formulation comprising 10 weight percents of the active tellurium containing compound (formulation PGB3) is soluble, dispersible and/or suspendable therein; and at the same time is chemically and physically stable upon storage at room temperature for at least 30 days, at least 60 days, at least 90 days, and even for 6 months, and is even stable upon storage at 40° C. for at least 30 days, and even as much as 90 days and more. In certain embodiments, formulations of the invention are provided as kits, which may include for example instructions for use and administration.

The phrase "chemically stable" refers to the absence of any chemical change in the tellurium-containing compound upon storage in dissolved or solid state. Examples of processes involving chemical change include, but are not limited to, hydrolysis, oxidation, etc. In particular, in view of the known findings that the tellurium-containing compounds exhibit an oxidative potential, processes involving chemical change may include redox reactions. Thus, in a "chemically stable" formulation, the various chemical components, especially the tellurium-containing compound, do not exhibit noticeable chemical change.

The phrase "physically stable" relates to the formation of insoluble and/or soluble aggregates as well as any structural deformation, discoloration and/or darkening of any of the formulation's ingredients. This phrase is further used herein with reference to maintenance of viscosity, resistance to syneresis, and in the case of emulsions, resistance to phase separation. Thus, a "physically stable" formulation, does not exhibit a noticeable change of its physical properties including solubility, color, viscosity, phase separation and the like.

Although the terms "chemically stable" and "physically stable" have been separately defined herein, they are not necessarily distinct, and may influence each other.

As demonstrated in the Examples section below, exemplary formulations according to the present embodiments were subjected to a thermal stability test, comprised of four daily temperature cycles of between −10° C. and 40° C., and lasting 48 hours. In another experiment, each sample was further placed in a 40° C. stability chamber for 90 days for an accelerated test.

Thus, the stability of the formulation may be defined based on its thermal stability, whereas according to a preferred embodiment of the present invention, the carrier is selected such that the formulation is stable upon cycling (mixing) at a temperature that alternates from about −10° C. to about 40° C. every 48 hours.

According to another preferred embodiment of the present invention, the carrier is selected such that the formulation is stable upon mixing (centrifugation) at about 3,000 RPM for about 10 minutes and then at about 10,000 RPM for about 10 minutes.

As demonstrated in the Examples section which follows, topical formulations containing 12% or 15% AS101 were prepared as semi-solid hydrophilic ointments (referred to herein as formulations PGB3 and PGB5, respectively), which are well suited for topical applications. The presently-developed formulations have good skin feeling, are easy to apply and do not have greasy or sticky characteristics. These formulations have successfully passed a set of accelerated instability physical tests. The chemical stability of AS101 was assessed by the lack of color change during the accelerated stability tests, since AS101 powder, or AS101 solution are known to become gray or black upon any minor oxidation (see, for example, Example 1).

Certain embodiments comprise about 12% AS101, about 13% AS101, about 14% AS101, and about 15% AS101. In other embodiments, topical formulations comprising AS101 in amounts of less than about 12% and greater than about 15% are used, including without limitation about 10%, about 11%, about 10% to about 12%, about 5% to about 10%, about 16%, about 17%, about 18%, about 19%, about 20%, about 12% to about 15%, about 15% to about 20%, about 20% to about 25%, about 25% to about 30%, about 30% to about 35%, and about 35% to about 40% AS101.

Solubilized or molecular forms of an active pharmaceutical ingredient are generally associated with better skin absorption in comparison to formulations in which the active ingredient is present in a crystalline form. In order to develop formulations comprising solubilized forms of tellurium-containing compounds, the solubility of these compounds was evaluated for a large variety of commonly used solvents.

As demonstrated in the Examples section that follows, although many pharmaceutically acceptable carriers have been tested in the course of experimentation, some were found incompatible. For example, as presented in Table 1 below, in the presence of solvents such as silicone oil and hydroxycellulose, which are generally accepted in cosmetic applications, undesirable coloration of the solution was observed, suggesting that the use these solvents as carriers for tellurium-containing compositions is limited.

Thus, any one or more carriers may be used in the preparation of the formulations of the present invention, provided they provide the chemical and physical stabilities described herein. This is readily detenninable following the chemical and physical stability tests described herein and exemplified in the examples section that follows.

As detailed in the Background section above, topical tellurium-containing formulations comprising C1-4 alkylene glycol carriers, such as polyethylene glycol (PEG), were mentioned only in passing, and no such stable formulations have been demonstrated. The use of C1-4 alkylene glycols, such as PEGs, as carriers in the preparation of stable topical formulations of tellurium-containing compounds has now been unexpectedly demonstrated. Thus, according to an exemplary embodiment of the present invention, the carrier comprises at least one C1-4 alkylene glycol. Preferably, the at least one alkylene glycol comprises a polyethylene glycol.

Polyethylene glycols are polymers of ethylene oxide having the general formula: $HO-CH_2-O-(CH_2-O-CH_2)$n-$OCH_2OH$ where n represents the number of oxyethylene groups and can be any integer from 1 to 100,000. The PEGs are designated by a numerical value, which is indicative of the average molecular weight for a given grade. PEGs having a molecular weight lower than 600 are liquids, and PEGs having molecular weights of above 1000 are solids at room temperature. PEGs are generally regarded as non-toxic and non-irritating.

According to a preferred embodiment of the present invention, the polyethylene glycol has an average molecular weight that ranges from about 100 to about 10,000.

As can be seen in the Examples section that follows, PEGs being within such a range of molecular weight were confirmed to be suitable as a carrier in topical formulations comprising tellurium-containing compounds.

As can be further seen in the Examples section that follows, in the preparation of topical formulations of the present invention, PEG 200, PEG 400 and PEG 4000 were used, and a combination thereof achieved a stable tellurium-containing formulation (see, Example 3).

Thus, according to an exemplary embodiment of the present invention, the polyethylene glycol is selected from the group consisting of PEG 200, PEG 400, PEG 4000 and any combination thereof.

According to another preferred embodiment of the present invention, the carrier comprises additional suitable carriers.

Since PEG molecular weights of below 600 are liquids, and since it is preferable that the tellurium-containing compound be at least partially liquidated, the formulation comprises at least one polyethylene glycol having an average molecular weight lower than 600. The concentration of the liquid PEGs (i.e., those having an average molecular weight lower than 600) preferably ranges from about 30 weight percents to about 90 weight percents of the total weight of the composition.

As can be seen in the Examples section that follows, a preferred formulation, according to the present invention, comprises about 39 weight percents PEG 200 and about 30 weight percents PEG 400. These formulations exemplify other embodiments comprising about 35 to 40 weight percent PEG 200 (e.g. 36%, 37%, 38%, 39%, and 40%), or about 30 to 50 weight percent PEG 200, and about 25 to 35 weight percent PEG 400 (e.g. 25%, 26%, 27%, 28%, 29%, 30%, 31%, 32%, 33%, 34%, and 35%). In certain preferred embodiments, the concentration of either PEG 200, or PEG 400, each ranges from about 10 weight percents to about 50 weight percents of the total weight of the composition.

However, while in topical formulations, it is often desirable to increase the viscosity of the formulation, and given that PEG molecular weights of above 1000 are solids at room temperature, at least one polyethylene glycol having an average molecular weight higher than 1000, can be advantageously added to the formulation. The concentration of a solid PEG (i.e., one having an average molecular weight higher than 1000) preferably ranges from about 5 weight percents to about 20 weight percents.

As can be seen in the Examples section below, a preferred formulation, according to the present invention, comprises about 10 weight percents of PEG 4000.

Thus, the preferred concentration of PEG 4000 ranges from about 5 weight percents to about 20 weight percents.

However, it should be evident to any person skilled in the art that other liquid and/or solid PEGS, such as, for example, PEG 150, PEG 200, PEG 600, PEG 1500, PEG 3500 and PEG 6000, as well as any combination thereof, are suitable for use in the context of the present embodiments, while selecting/composing the desired consistency of the formulation.

Thus, various. PEGs, having various molecular weights, can be selected so as achieve the desired consistency of the formulation (e.g., in terms of viscosity, as is detailed hereinbelow), the desired convenience to topically apply the formulation, and the desired absorbance of the composition, as is further discussed in detail hereinbelow.

All of these concentrations given hereinabove comply with the inactive ingredients guideline limits as published by the FDA and by the European authorities.

The formulations described herein can optionally further comprise a variety of components that are suitable for providing the compositions with additional usage benefits. Such conventional optional components are well known to those skilled in the art and are referred to herein as "ingredients". Some non-limiting representative examples of these ingredients include penetration enhancers, stabilizers, humectants, deodorants, aroma modifiers, antiperspirants, sun screening agents, sunless tanning agents, hair conditioning agents, pH adjusting agents, chelating agents, preservatives, emulsifiers, occlusive agents, emollients, thickeners, solubilizing agents, anti-irritants, colorants, propellants and surfactants.

It should be noted, however, that the additional ingredients are selected suitable (compatible) for being formulation in combination with the tellurium-containing compound.

In the course of the studies described herein, it has been found that upon addition of certain ingredients, a formulation having enhanced stability was obtained. Thus, for example, it has been found that upon adding propylene glycol to the tellurium-containing compound, no decomposition, coloration or any other adverse feature was observed during the formulation process and the following storage. Additionally, it was found that the presence of relatively low amounts of DMSO (about 5%) in the formulation, rendered it highly stable. Both propylene glycol and DMSO are recognized herein as highly effective penetration enhancers and hence their inclusion as additives in the formulation is highly beneficial.

Other substances that can act as stabilizing agents of the tellurium-containing compounds and/or of residual (ppm) amounts of impurities thereof can be included in the formulations described herein. Alternatively, stabilizers, which affect the formulation stability in terms of its uniformity, smoothness and consistency, are preferably included within the formulation described herein. Such stabilizers can be, for example, non-ionic, anionic, cationic and/or amphiphilic surfactants. Preferably, the stabilizer is a non-ionic surfactant such as, but not limited to, polyethoxylated fatty alcohols and glycerol derivatives. Representative examples of surfactants include, without limitation, Tweens, tritons, tyloxapol, pluronics, Brijes, Spans, poloxamers and emulphors. A particularly presently preferred exemplary surfactant is a polyethoxylated fatty alcohol marketed under the trademark "BRIJ" by ICI Americas, Inc.

Alternatively, the stabilizer is an anionic surfactant such as, but not limited to, alkyl and aryl sulphonate or phosphate. Also alternatively, the stabilizer is a cationic surfactant such as cetyl pyridinium chloride or bromide, and cetyl trimethylammonium bromide. Alternatively and preferably, the stabilizer is an amphiphilic surfactant such as, but not limited to, alkyl betaine derivatives, cocoamphodiacetale derivatives, lauroamphoacetates and phosphatidylglycerol.

In addition, as mentioned hereinabove, the formulations described herein can comprise penetration enhancers. As is well known in the art, a penetration enhancer is a compound capable of enhancing the transdermal penetration of an active ingredient through the skin layer. Suitable penetration enhancers which are usable in context of the present invention include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), PHOSAL®, glycerol monolaurate (GML), lecithin, the 1-substituted azacycloheptan-2-ones, particularly 1-n-dodecylcyclazacycloheptan-2-one, alcohols, and the like. The penetration enhancer may also be a vegetable oil. Such oils include, for example, safflower oil, cottonseed oil and corn oil. Preferable penetration enhancers, as exemplified below, are propylene glycol and PHOSAL 50PG™.

Representative examples of humectants that are usable in this context of the present invention include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, sugars and starches, sugar and starch derivatives (e.g., alkoxylated glucose), hyaluronic acid, lactamide monoethanolamine, acetamide monoethanolamrine and any combination thereof.

The compositions of the present invention can further comprise a pH adjusting agent. The addition of a pH-adjusting agent is particularly preferred when the compositions are applied topically on the skin. The pH of these treated areas is typically lower than 6.0. Hence, it is preferable for the compositions of the present invention to have a pH value of between about 4 and about 7, preferably between about 4 and about 6, so as to avoid irritations to the skin or induction of imbalance of the bacteria population of the genital areas. Suitable pH adjusting agents include, for example, one or more of adipic acids, glycines, citric acids, calcium hydroxides, magnesium aluminometasilicates, buffers or any combinations thereof.

Representative examples of deodorant agents that are usable in the context of the present invention include, without limitation, quaternary ammonium compounds such as cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmlthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

Antiperspirant agents can be incorporated in the compositions of the present invention either in a solubilized or a particulate form and include, for example, aluminum or zirconium astringent salts or complexes.

Representative examples of sun screening agents usable in context of the present invention include, without limitation, p-aminobenzoic acid, salts and derivatives thereof (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene boman-2-one) and 4-isopropyl-di-benzoylmethane, and any combination thereof.

Representative examples of sunless tanning agents usable in context of the present invention include, without limitation, dihydroxyacetone, glyceraldehyde, indoles and their derivatives. The sunless tanning agents can be used in combination with the sunscreen agents.

The chelating agents are optionally added to the compositions of the present invention so as to enhance the preservative or preservative system. Preferred chelating agents are mild agents, such as, for example, ethylenediaminetetraacetic acid (EDTA), EDTA derivatives, or any combination thereof.

Suitable preservatives that can be used in the context of the present composition include, without limitation, one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof.

Suitable emulsifiers that can be used in the context of the present invention include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Suitable occlusive agents that can be used in the context of the present invention include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppy seed oil, pine oil, castor oil, soybean oil, avocado oil, safflower oil, coconut oil, hazelnut oil, olive oil, grape seed oil and sunflower seed oil.

Suitable emollients, that can be used in the context of the present invention include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners that can be used in the context of the present invention include, for example, non-ionic water-soluble polymers such as hydroxyethylcellulose (commercially available under the Trademark NATROSOL® 250 or 350), cationic water-soluble polymers such as Polyquat 37

(commercially available under the Trademark SYNTHALEN), fatty alcohols, fatty acids and their alkali salts and mixtures thereof.

Representative examples of solubilizing agents that are usable in the context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEENS and SPANS, e.g., TWEEN 80. Other solubilizers that are usable for the compositions of the present invention are, for example, polyoxyethylene sorbitan fatty acid ester, polyoxyethylene n-alkyl ethers, n-alkyl amine n-oxides, poloxamers, organic solvents, phospholipids and cyclodextrines.

Suitable anti-irritants that can be used in the context of the present invention include, for example, steroidal and non steroidal anti-inflammatory agents or other materials such as aloe vera, chamomile, alpha-bisabolol, cola nitida extract, green tea extract, tea tree oil, licorice extract, allantoin, caffeine or other xanthines, glycyrrhizic acid and its derivatives.

It is important to note that some inactive ingredients, such as silicone oils and cellulose polymers, which are common additives in the cosmetic industry, were found to react with the tellurium-containing compound, causing unaccepted change of color (see Example 2).

The formulations of the present invention may further include one or more additive(s), such as, but not limited to, fillers, salts, sugars and/or glycerin. These additives are typically added to the formulation to reinforce the mechanical strength thereof, to alter the diffusion or absorbency properties of it and/or to improve the cost-efficiency of the product.

In addition to the tellurium-containing compounds described above, the formulations described herein can further comprise an additional active agent to provide an additive beneficial effect in terms of the ailment being treated, conditions associated with the ailment being treated or other parameters such as psychological effects and prophylactic effects.

Thus, according to an additional embodiment of the present invention, each of the formulations described herein may further comprise an additional active agent, known to be used for treating medical conditions treated by topical formulations of tellurium-containing compounds, as described hereinbelow.

The additional active agent can be, for example, an antibiotic agent, an antimicrobial agent, an anti-acne agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, a chemotherapeutic agent, an antidepressant, an anti histamine, a vitamin, a hormone, a keratolytic agent and an antidandruff agent. The active agent is selected suitable for being combined with the tellurium-containing compound in terms of its compatibility.

Suitable anti-acne agents for use in this context of the present invention include, without limitation, keratolytics such as salicylic acid, sulfur, glycolic, pyruvic acid, resorcinol, and N-acetylcysteine and retinoids such as retinoic acid and its derivatives (e.g., cis and trans, esters).

Suitable antibiotics for use in this context of the present invention include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Representative examples of non-steroidal anti-inflammatory agents that are usable in this context of the present invention include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable antipruritic agents include, without limitation, pharmaceutically acceptable salts of methdilazine and trimeprazine.

Non-limiting examples of anesthetic drugs that are suitable for use in context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erytiromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fuimaric acid and its salts, lysine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in context of the present invention include norepinephrine-reuptake inhibitors ("NRIs"), selective-serotonin-reuptake inhibitors (SSRIs), monoamine-oxidase inhibitors (MAOIs), serotonin-and-noradrenalin-reuptake inhibitors ("SNFIs"), corticotropin-releasing factor (CRF) antagonists, α-adrenoreceptor antagonists, NK1-receptor antagonists, $5-HT_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Exemplary anti-dandruff ingredients usable in context of the present invention include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopirox olamine, and mixtures thereof.

Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of dermatological active ingredients usable in context of the present invention include jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate. Non-limiting examples of antifungal agents include miconazole, clotrimazole, butoconazole, fenticonasole, tioconazole, terconazole, sulconazole, fluconazole, haloprogin, ketonazole, ketoconazole, oxinazole, econazole, itraconazole, terbinatine, nystatin and griseofulvin.

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

Suitable hormones for use in the context of the present invention include, for example, androgenic compounds and progestin compounds.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

By selecting the appropriate carrier and optionally other ingredients that can be included in the composition, as is detailed hereinabove, the tellurium-containing compounds used in context of the present invention may be formulated into any form typically employed for topical application. Hence, the formulations of the present invention can be, for example, in a form of a cream, an ointment, a paste, a gel, a lotion, a milk, a suspension, an aerosol, a spray, a foam, a shampoo, a hair conditioner, a serum, a swab, a pledget, a pad, a patch and a soap.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark CARBOPOL™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Compositions for topical or systemic application, which contain one or more of the tellurium-containing compounds described herein and optionally pharmaceutically acceptable carriers and excipients, are formulated as creams, lotions, ointments, gels, solutions, foams, mousses and the like (as is detailed hereinabove), using conventional methods (see, for example, Harry's Cosmeticology, Seventh Edition, Edited by J B Wilkinson and R J Moore, Longmann Scientific & Technical, 1982, Chapter 13 "The Manufacture of Cosmetics" pages 757-799; and "Remington's Pharmaceutical Sciences," Mack Publishing Co., Easton, Pa., latest edition).

The compositions of the present invention may be packed or presented in any convenient way. For example, they may be packed in a tube, a bottle, or a pressurized container, using techniques well known to those skilled in the art and as set forth in reference works such as Remington's Pharmaceutical Science 15$^{th}$ Ed. It is preferred that the packaging is done in such a way so as to minimize contact of the unused compositions with the environment, in order to minimize contamination of the compositions before and after the container is opened.

The formulations are preferably identified in print, in or on the packaging material, for use in the treatment of any medical conditions in which topical application of a tellurium-containing compound is beneficial.

An exemplary formulation according to the present embodiments comprises a combination of various polyethylene glycols propylene glycol and/or DMSO, PHOSAL®50PG™ and Brij 72. Formulations comprising these components were found to be homogeneous and had very fine particles as seen under polarized light (see, for example, formulation PGB3 in FIGS. 3A and 3B), and were further found to be stable and to withstand a series of stability tests while not separating or discoloring, and further while maintaining their viscosity at ambient temperature.

It has thus been demonstrated herein for the first time that tellurium-containing compounds can be formulated in a topical aqueous formulation, also at relatively high concentrations, while maintaining their chemical, physical and visual stability, as well as an optimal stability, resulting in a smooth and pleasant feel.

Being hydrophilic, these formulations are non-greasy, and will not stain the cloths or garments coming in contact with them.

Thus, according to a preferred embodiment of the present invention, any of the above-detailed formulations is provided as a hydrophilic formulation.

According to another preferred embodiment of the present invention, any of the above-detailed formulations is provided as a washable formulation.

These formulations are further characterized by maintaining their viscosity upon various conditions.

Thus, according to a preferred embodiment of the present invention, each of the formulations described herein are characterized by a viscosity in the range of from 1,000 to 1,000,000 cpi at room temperature, preferably, from about 3,000 to about 30,000 cpi at room temperature.

As used herein, the term "about" describes ±10%.

In each of the formulations described herein, a concentration of the tellurium-containing compound in the formulation preferably ranges from about 0.01 weight percent to about 50 weight percents, more preferably from about 1 weight percent to about 20 weight percents, of the total weight of the composition. In certain embodiments, the tellurium-containing compound in the formulation is present in an amount up to about 25 weight percent.

Thus, depending on the condition being treated and the composition form, the concentration of the tellurium-containing compound can be, for example, at least 0.01 weight percent, at least 0.05 weight percent, at least 0.1 weight percent, at least 0.5 weight percent, at least 1 weight percent, at least 2 weight percents, at least 3 weight percents, at least 4 weight percents or at least 5 weight percents. Higher concentrations can also be used and thus can be, for example, at least 5 weight percents, at least 6 weight percents, at least 7 weight percents, at least 8 weight percents, at least 9 weight percents or at least 10 weight percents and up to at least 20 weight percents, at least 25 weight percents, at least 30 weight percents, at least 40 weight percents, at least 50 weight percents, at least 60 weight percents, at least 70 weight percents, at least 80 weight percents, and can be up to about 85 weight percents of the total weight of the composition.

In an exemplary formulation, the tellurium-containing compound is present in a concentration of 12 weight percents. In another exemplary formulation, the tellurium-containing compound is present in a concentration of 15 weight percents.

As described in the Background section hereinabove, topical formulations are often characterized by high concentrations of the active ingredient, typically higher than 1 weight percent, and preferably higher than 5 weight percents, which are required to provide the desired therapeutic effect. To date, tellurium-containing compositions having such a relatively high concentration of the tellurium-containing compound were characterized by insufficient suitability for topical applications in terms of stability and appearance. As shown herein, tellurium-containing topical formulations can be readily obtained and are characterized by a high stability even at high concentrations typical of topical formulations.

Thus, further according to the present invention there is provided a chemically and physically stable formulation for topical application, which comprises a tellurium-containing compound as described herein, in a concentration of at least 3 weight percents, and a pharmaceutically acceptable carrier. Often in the treatment of psoriasis and related skin disorders the active ingredient comprises 3-4 weight percents of the formulation.

Preferably the formulation comprises at least 3 weight percents, more preferably at least 4 weight percents, more preferably at least 5 weight percents, more preferably at least 6 weight percents, more preferably at least 7 weight percents, more preferably at least 8 weight percents, more preferably at least 9 weight percents, more preferably at least 10 weight percents, more preferably at least 11 weight percents, more preferably at least 12 weight percents, more preferably at least 13 weight percents, more preferably at least 14 weight percents, more preferably at least 15 weight percents, more preferably at least 16 weight percents, more preferably at least 17 weight percents, more preferably at least 18 weight percents, more preferably at least 19 weight percents, and more preferably at least 20 weight percents, The formulations of the present invention may be manufactured by processes well known in the art, e.g., by means of conventional mixing, dissolving, granulating, dragee-making, levigating, emulsifying, encapsulating, entrapping or lyophilizing processes.

According to another aspect of the present invention, the formulations described herein are easily prepared by mixing a tellurium-containing compound and a carrier, as these are defined herein. Preferably, the mixing is conducted at a temperature range of about 10° C. to about 100° C.

As exemplified in the Background section hereinabove, tellurium-containing compounds were found exceptionally effective in treating skin and mucosal membrane ailments, caused by HPV (WO 2005/069735, supra), in the treatment or prevention of alopecia and other conditions associated with hair loss (U.S. Provisional Patent Application No. 60/610,660, supra, U.S. Pat. Nos. 6,552,089 and 5,262,149 supra), in the treatment of BCC and AK (U.S. Provisional Patent Application No. 60/716,923, supra), in the treatment of damages caused by exposure to UV irradiation (U.S. Provisional Patent Application No. 60/716,924, supra), psoriasis (U.S. Pat. No. 6,472,381), atopic dermatitis, Kaposi's sarcoma, scleroderma, burns, scarring (see U.S. Provisional Patent Application No. 60/610,660) and metastatic melanoma (Sun et al. 1996, supra).

Thus, medical conditions treatable by the tellurium-containing formulations include, for example, scleroderma, psoriasis, atopic dermatitis, scarring, a human papilloma virus related skin and/or mucosal membrane ailment, condilloma, warts, alopecia, hair loss, metastatic melanoma, basal cell carcinoma, actinic keratosis and UV skin damage.

The term "scleroderma" refers to a disease of the skin and connective tissue that causes the skin to become hard and can result in hair loss.

The term "atopic dermatitis" is also known as eczema, and refers to an allergic skin disorder that us causes the skin to itch, scale and flake.

The term "scarring" refers to a biologic process of wound repair in the skin and other tissues of the body. It considered that almost every wound (e.g. after accident, disease, or surgery) results in some degree of scarring.

The term "melanoma" refers to a malignant tumor of the skin, which often appears as a slightly raised irregular brownish tumor.

The term "Kaposi's sarcoma" (KS) refers to a tumor which appears as a flat or raised purplish patch on the skin or mucous membranes (in the mouth, rectum, or vagina). KS may also spread to internal organs, like the esophagus, intestines, colon, or lungs.

As used herein, the phrase "a skin or mucosal membrane ailment caused by a HPV", which also referred to herein interchangeable as "HPV-caused ailment", encompasses any ailment that is associated, either directly or indirectly, with any type of HPV.

To date, there are more than seventy identified distinct types of HPVs. These different types have been subdivided into two large categories: cutaneous and mucosal. Since, as is further discussed hereinabove, some HPV-caused ailments may develop into cervical cancer, these different virus types have been further categorized in this respect by their risk grade and therefore include low-risk HPV types, moderate-risk HPV types and high-risk HPV types.

According to still further features in the described preferred embodiments the skin or mucosal membrane ailment is such as, but not limited to verruca vulgaris, plantar warts, palmar warts, periungal warts, planar warts, mosaic warts, genital warts, venereal warts (condylomata acuminata), butcher's warts, malignant epidermodyspasia verruciformis, advanced intraepithelial dysplasia, cervical cancer, mepidermodysplasia verruciformis, cutaneous warts in immunosuppressive patients, laryngeal papillomas and oral papilloma.

However, it is expected that during the life of this patent many relevant medical conditions will be found to be treatable by tellurium-containing topical formulations, and thus the scope of the phrase "for use in the treatment of any medical conditions in which topical application of a tellurium-containing compound is beneficial" is intended to include all such new medical conditions a priori.

As used herein, the phrase "tellurium-containing compound" encompasses any compound that includes one or more tellurium atoms.

The tellurium-containing compound may be an inorganic compound or an organic compound.

Inorganic tellurium-containing compounds include, for example, tellurium dioxide ($TeO_2$) per se.

Organic tellurium-containing compounds may be in the form of an organic complex such as, for example, a $TeO_2$ complex with citric acid or ethylene glycol, which may form $TeO_2$ as an end product in aqueous solutions. A representative example of the latter is the complex $TeO_2HOCH_2CH_2OHNH_4Cl$. Otherwise, the tellurium-containing compounds described herein include one or more tellurium atoms and one or more organic moieties that are attached thereto, for example, ammonium salts, or any other salts, of halogenated tellurium-containing compounds having a bidentate cyclic moiety attached to the tellurium atom. The bidentate cyclic moiety is preferably a di-oxo moiety having two oxygen atoms attached to the tellurium atom. The bidentate cyclic moiety can be a di-thio moiety, in which two sulfur atoms are attached to the tellurium atom.

Preferred compounds in this category are collectively represented by the general Formula I:

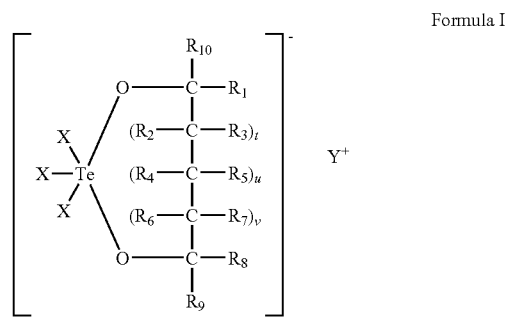

Formula I

In the general Formula I above, each of t, u and v is independently 0 or 1, such that the compound may include a five-membered ring, a six-membered ring, or a seven-membered ring. Preferably, each of t, u and v is 0, such that the compound includes a five-membered ring.

X is a halogen atom, as described hereinabove, and is preferably chloro.

In some embodiments, Y is a cation. In a preferred embodiment, Y is selected from the group consisting of ammonium, phosphonium, potassium, sodium and lithium, and is preferably ammonium.

Each of $R_1$-$R_{10}$ is independently selected from the group consisting of hydrogen, hydroxyallcyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido.

As used herein, the term "alkyl" refers to a saturated aliphatic hydrocarbon including straight chain and branched chain groups. Preferably, the alkyl group has 1 to 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. When substituted, the substituent group can be as described herein for $R_1$.

As used herein, the term "hydroxyalkyl" refers to an alkyl, as this term is defined herein, substituted by a hydroxy group, as defined herein, and includes, for example, hydroxymethyl, hydroxyethyl, hydroxypropyl and hydroxy-n-butyl.

As used herein, the term "halogen", which is also referred to herein interchangeably as "a halogen atom" or "halo", includes chloro (Cl), bromo (Br), iodo (I) and fluoro (F).

The term "haloalkyl" refers to an alkyl as this term is defined herein, substituted by a halogen, as defined herein, and includes, for example, chloromethyl, 2-iodoethyl, 4-bromo-n-butyl, iodoethyl, 4-bromo-n-pentyl and the like.

The term "alkanoyloxy" refers to a carbonyl group, as define herein and includes, for example, acetyl, propionyl, butanoyl and the like.

The term "carboxyalkyl" refers to an alkyl, as this term is defined herein, substituted by a carboxy group, as defined herein, and includes, for example, carboxymethyl, carboxyethyl, ethylenecarboxy and the like.

The term "alkylcarbonylallcyl" refers to an alkyl, as this term is defined herein, substituted by a carbonyl group, as defined herein, and includes, for example, methanoyhnethyl, ethanoylethyl and the like.

The term "amidoalkyl" refers to an alkyl, as this term is defined herein, substituted by an amide group, as defined herein, and includes, for example, —$CH_2CONH_2$; —$CH_2CH_2CONH_2$; —$CH_2CH_2CH_2CONH_2$ and the like.

The term "cyanoalkyl" refers to an alkyl, as this term is defined herein, substituted by an cyano group, as defined herein, and includes, for example, —$CH_2CN$; —$CH_2CH_2CN$; —$CH_2CH_2CH_2CN$ and the like.

The term "N-monoalkylamidoalkyl" refers to an alkyl, as this term is defined herein, substituted by an amide group, as defined herein, in which one of R' and R" is an alkyl, and includes, for example, —$CH_2CH_2CONHCH_3$, and —$CH_{—2}CONHCH_2CH_3$.

The term N,N-dialkylamidoalkyl refers to an alkyl, as this term is defined herein, substituted by an amide group, as defined herein, in which both R' and R" are alkyl, and includes, for example, —$CH_2CON(CH_3)_2$; $CH_2CH_2CON(CH_2—CH_3)_2$ and the like.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be as described herein for R1.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be as described herein for R1.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, faran, thiophene, imidazole, oxazole, thiazole, pyrazole, pyridine, pyrimidine, quinoline, isoquinoline and purine. The heteroaryl group may be substituted or unsubstituted. When substituted, the substituent group can be described herein for R1.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituent group can be as described herein for R1.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyd, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein.

A "carboxy" group refers to a —C(=O)—O—R' or a —O—C(=O)—R' group, where R' is as defined herein.

A "sulfinyl" group refers to an —S(=O)—R' group, where R' is as defined herein.

A "sulfonyl" group refers to an —S(=O)$_2$—R' group, where R' is as defined herein.

A "sulfate" group refers to a —O—S(=O)$_2$—OR' group, where R' is as defined herein.

A "sulfonamido" group refers to a —S(=O)$_2$—NR'R" group or a R'S(=O)$_2$—NR", with R' is as defined herein and R" is as defined for R'.

A "carbamyl" or "carbamate" group refers to an —OC(=O)—NR'R" group or a R"OC(=O)—NR'— group, where R' and R" are as defined herein.

A "thiocarbamyl" or "thiocarbamate" group refers to an —OC(=S)—NR'R" group or an R"OC(=S)NR'— group, where R' and R" are as defined herein.

An "amino" group refers to an —NR'R" group where R' and R" are as defined herein.

An "amido" group refers to a —C(=O)—NR'R" group or a R'C(=O)—NR" group, where R' and R" are as defined herein.

A "nitro" group refers to an —$NO_2$ group.

A "cyano" group refers to a —C≡N group.

The term "phosphonyl" describes a —O—P(=O)(OR')(OR") group, with R' and R" as defined hereinabove.

The term "phosphinyl" describes a —PR'R" group, with R' and R" as defined hereinabove.

As cited hereinabove, the compounds in this category are salts of organic tellurium-containing compounds. The salts can be, for example, ammonium salts, phosphonium salts and alkaline salts such as potassium salts, sodium salts, lithium salts and the like.

Hence, Y in Formula I above can be a phosphonium group, as defined herein, an ammonium group, as defined herein, potassium ($K^+$), sodium $Na^+$) or lithium ($Li^+$).

As used herein, the term "phosphonium" describes a —$P^+R'R"R'''$ group, with R' and R" as defined herein and R''' is as defined for R'. The term "phosphonium", as used herein, further refers to a —$P^+R_6$ group, wherein each of the six R substituents is independently as defined herein for R, R" and K'''.

The term "ammonium" describes a —$N^+R'R"R'''$ group, with R', R" and R''' as defined herein.

More preferred compounds in this category include compounds having the general Formula I described above, in which Y is ammonium or phosphonium, t, u and v are each 0, and each of $R_1$, $R_8$, $R_9$ and $R_{10}$ is independently hydrogen or alkyl. These compounds can be represented by the following structure:

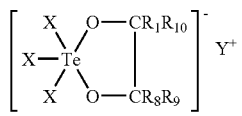

wherein each of $R_1$, $R_8$, $R_9$ and $R_{10}$ is independently hydrogen or alkyl, whereas a preferred alkyl is methyl, and X is halogen, preferably chloro.

The presently most preferred compound for use in the context of the present invention has the following structure:

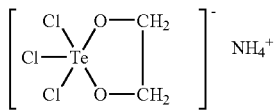

This compound is ammonium trichloro(dioxyethylene-O,O')tellurate, which is also referred to herein and in the art as AS101.

Additional representative examples of organic tellurium-containing compound that are suitable for use in the context of the present invention include halogenated tellurium having a bidentate cyclic moiety attached to the tellurium atom. The bidentate cyclic moiety is preferably a di-oxo ligand having two oxygen atoms attached to the tellurium atom. Alternatively, the bidentate cyclic moiety can be a di-thio ligand, in which two sulfur atoms are attached to the tellurium atom.

Preferred compounds in this category can be represented by the general Formula II:

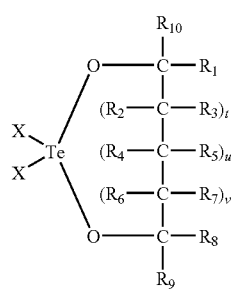

Formula II wherein t, u, v, X and $R_1$-$R_{10}$ are as defined hereinabove.

More preferred compounds are those in which t, u, and v are each 0, and X is chloro, such as, but not limited to, the compound having the following structure:

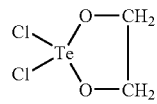

The above compound is also known and referred to herein as AS103.

The organic tellurium-containing compounds having Formulae I and II can be readily prepared by reacting tetrahalotelluride such as $TeCl_4$ with a dihydroxy compound, as is described in detail in U.S. Pat. Nos. 4,752,614, 4,761,490, 4,764,461 and 4,929,739, which are incorporated by reference as if fully set forth herein.

Additional representative examples of organic tellurium-containing compounds that are suitable for use in the context of the present invention include compounds in which two bidentatic cyclic moieties are attached to the tellurium atom. Preferably, each of the cyclic moieties is a di-oxo moiety. Alternatively, one or more of the cyclic moieties is a di-thio moiety.

Preferred compounds in this category are collectively represented by the general Formula III:

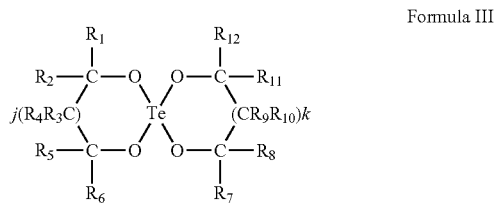

Formula III

In the general Formula III above, each of j and k is independently an integer from 0 to 4, such that the compound may include a five-membered ring, a six-membered ring, a seven-membered ring, an eight-membered ring and/or a nine-membered ring. Preferably, each of j and k is an integer from 0 to 2, such that the compound includes a five-membered ring, a six-membered ring and/or a seven-membered ring, More preferably, each of j and k is 0.

$R_1$-$R_{12}$ are as defined hereinabove for $R_1$-$R_{10}$.

More preferred compounds in this category are those in which j and k are each 0, and $R_3$, $R_4$, $R_9$ and $R_{10}$ are each hydrogen, having the following structure:

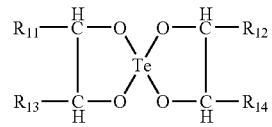

wherein each of $R_{11}$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido, as these terms are defined herein.

The most preferred compound in this category is a compound in which each of $R_{11}$-$R_{14}$ is hydrogen. This compound is also known as AS102.

Additional representative examples of organic tellurium-containing compounds that are suitable for use in the context of the present invention include the recently disclosed ditellurium compounds having general Formula IV:

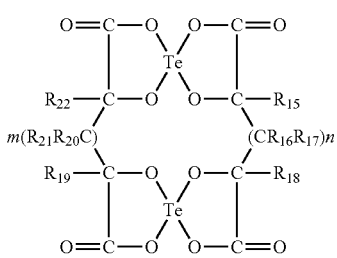

Formula IV wherein each of $R_{15}$-$R_{22}$ is independently selected from the group consisting of hydrogen, hydroxyalkyl, hydroxy, thiohydroxy, alkyl alkenyl, alkynyl, alkoxy, thioalkkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido, as these terms are defined herein; and m and n are each an integer from 0 to 3.

Preferred compounds in this category are those in which m and n are each 0.

The presently most preferred compound in this family is a compound in which $R_{15}$, $R_{18}$, $R_{19}$ and $R_{22}$ are all hydrogen, referred to hereinafter as SAS, and which has the following structure:

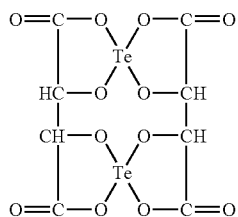

According to a most preferred embodiment of the present invention, the tellurium-containing compound is of Formula 1, most preferably, in which Y is ammonium, t, u and v are each 0, and each of $R_1$, $R_8$, $R_9$ and $R_{10}$ is independently methyl and X is chloro, also known as AS101.

As demonstrated in the Examples section which follows, topical formulations comprising AS101, as an exemplary tellurium-containing compound, were formed (Example 3, formulation PGB3) and were found to be well solubilized (FIGS. 3A and 3B) as well as highly stable, upon being subjected to a series of thermal stability, visual and centrifugation tests.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

AS101 was supplied by M. Albeck from the chemistry department at Bar Ilan University, in three forms: as a powder, as a 20% solution in dimethyl sulfoxide (DMSO) and as an ointment containing the DMSO solution in combination with petroleum jelly.

Microscopic Evaluation of Samples and Polarized Light Crystallography: Formulation Stability Measurements Thermal Stability:

each formulation sample was placed in a plastic eppendorf tube and rotated each day between −10° C. and 40° C. four times, each cycle lasted 48 hours. Each sample was further placed in a 40° C. stability chamber for 90 days for an accelerated test.

Centrifugation:

each formulation sample was placed in a plastic eppendorf tube and centrifuged for 10 minutes at 3,000 RPM and then for 10 minutes at 10,000 RPM.

Example 1

Characterization of AS101 Powder, Solution and Ointment

In order to evaluate the effect of the present formulations of AS101 on its crystallinity and solubility, three samples of AS101 were tested: a powder, a 20% (by weight) solution in DMSO and an ointment containing the DMSO solution in combination with petroleum jelly.

FIGS. 1A-B present images of the content and packaging components of the containers in which the AS101 powder (FIG. 1A) and the 20% AS101 20% solution in DMSO (FIG. 1B) were provided, upon 30 days of storage at ambient temperature.

Samples were further characterized by polarized light and the obtained images 5 are presented in FIGS. 2A-B.

AS101 Powder:

The white crystalline coarse powder was placed in a scintillation glass bottle with a non-sealed cap. After storage, the aluminum laminate cap was examined and appeared to be chemically and physically decomposed, with black particles of its internal lining falling into the powder (FIG. 1A). The AS101 powder was characterized as having particles of about 20-40 microns in diameter, and distinct crystals producing birefrigerence under polarized light, as seen in FIG. 2A.

AS101 Solution in DMSO:

A 20% (by weight) solution of AS101 in DMSO was prepared. The solution appeared as a yellow liquid with a cloudy dispersion evolving upon mixing. After placing it in a scintillation glass bottle with a non-sealed cap, and re-examining the aluminum laminate cap after storage, decomposition was observed, as can be seen in FIG. 1B. As shown in FIG. 2B, no crystals were detected under polarized light. However, some unidentified particles were observed.

AS101 Ointment:

A 20% solution of AS101 in DMSO was mixed with petroleum jelly to yield a white waxy material having a small amount of liquid on top. FIGS. 2C and 2D show two samples of the AS101 ointment under polarized light, confirming that AS101 was solubilized in DMSO but was not solubilized in the DMSO/petroleum jelly ointment, re-crystallizing into another polymorphic type.

Example 2

AS101 Solubility Profile

In a search for an improved formulation for topical application, the solubility and stability (by coloration detection) of AS101 in various hydrophilic and lipophilic solvents were determined. Since it is commonly known that topically applied formulations have better skin absorption and feel when the active pharmaceutical ingredient is solubilized or is in a molecular form, a desirable topical formulation should be characterized by high solubility and/or dispersability of the active ingredient therein.

Thus, solutions containing 10% by weight of AS101 in each solvent, were prepared by mixing AS101 in the solvent at ambient temperature. The solubility and coloration results, as observed after 24 hours, are presented in Table 1 below.

TABLE 1

| Solvent | Solubility | Coloration |
|---|---|---|
| DMSO | Yes | No |
| Butyleneglycol | Yes | No |
| PEG 400 | Yes | No |
| PEG 200 | Yes | No |
| Glycofurol | Yes | No |
| Propylene Glycol | Yes | No |
| Transcutol | Yes | No |
| IPM | No | No |
| Mineral oil | No | No |
| MCT oil | No | No |
| Arlamol E | No | No |
| Hexylene glycol | No | No |
| DMI | No | No |
| Alkyl benzoate | No | No |
| 1% acetic acid | No | No |
| Silicone oil | No | Black |

As shown in Table 1, AS101 was well solubilized in amphiphilic glycolic solvents such as PEG, butyleneglycol, gycofurol, propylene glycol and TRANSCUTOL (diethylene glycol mononethyl ether), while no precipitation or re-crystallization of AS101 was observed during the tested period.

Furthermore, solvents such as silicone oil and hydroxycellulose, which are commonly-used inactive ingredients that improve the skin feeling of cosmetic formulations, provide topical formulations with beneficial properties such as pleasant skin feeling, were found incompatible due to unacceptable solution coloration.

Since AS101 is well solubilized in various PEGs and does not precipitate or re-crystallize at ambient temperature, further studies have focused on the use of PEG mixtures as an exemplary carrier of choice.

Example 3

AS101 Formulations

AS101 formulations were developed based on the solubilization of AS101 in a mixture of PEG solvents, PEG 200 and PEG 400, whereas the concentration of each PEG solvent was selected so as to comply with the inactive ingredients guideline limits as published by the FDA. PEG 4000 was added to modify the viscosity of the formulation to a topical use.

In one exemplary formulation, propylene glycol and PHOSAL® 50PG™ were added. Propylene glycol was also found to stabilize the formulation.

Such an Exemplary formulation (hereinafter termed PGB3) is presented in Table 2 below:

TABLE 2

| Component | Weight % | Proposed Function |
|---|---|---|
| AS101 | 12.00 | Active ingredient |
| PEG-400 | 39.00 | Solvent/carrier |
| PEG-200 | 30.00 | Solvent/carrier |
| PEG-4000 | 10.00 | Thickener |
| Propylene glycol | 5.00 | Co-solvent |
| PHOSAL ® 50PG | 2.00 | Skin penetrant |
| Brij 72 | 2.00 | Stabilizer |
| Total | 100.00 | |

All glass or Teflon beakers, stirrers and mixer heads were used in the preparation of AS101 formulations. PEG-400, PEG-200 and propylene glycol were heated in a glass beaker on a steam bath to 80° C.-85° C., while moderately mixing. AS101 was then added, while moderately mixing to ensure visual turbulence. Mixing was continued until AS101 was completely dissolved, Brij and PEG-4000 were added thereafter, and further mixing was effected until a homogenous solution was observed. The mixture was then removed from the steam bath and was left to cool down, while stirring was continued. At about 50° C., PHOSAL® was added and mixing was continued until a homogeneous solution was obtained. The obtained formulation was stored in plastic, metal-free tubes/closures.

In an alternative procedure, propylene glycol was first added to AS101, while moderately mixing to ensure visual turbulence. Mixing was continued until AS101 was completely dissolved, Brij and PEGS were added thereafter, and further mixing was effected until a homogenous solution was observed.

Upon heating the mixture of AS101 and propylene glycol, no change was observed.

A similar placebo formulation (hereinafter termed PGB3P) was prepared in a similar manner, by not adding the AS101 to the mixture.

Figure 3:
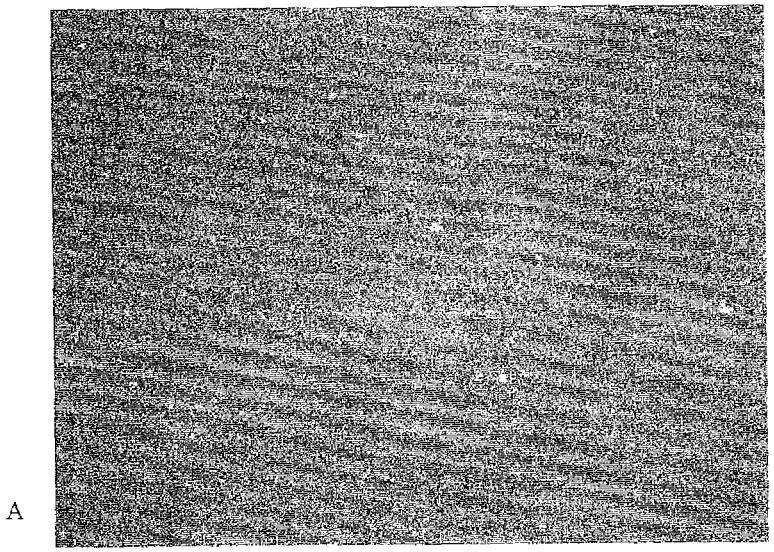
FIGS. 3A and 3B present images of the tellurium-containing PGB3 formulation, according to preferred embodiments of the present invention, under polarized light at ×100 magnification (FIG. 3A) and at ×400 magnification (FIG. 3B).
Figure 3:
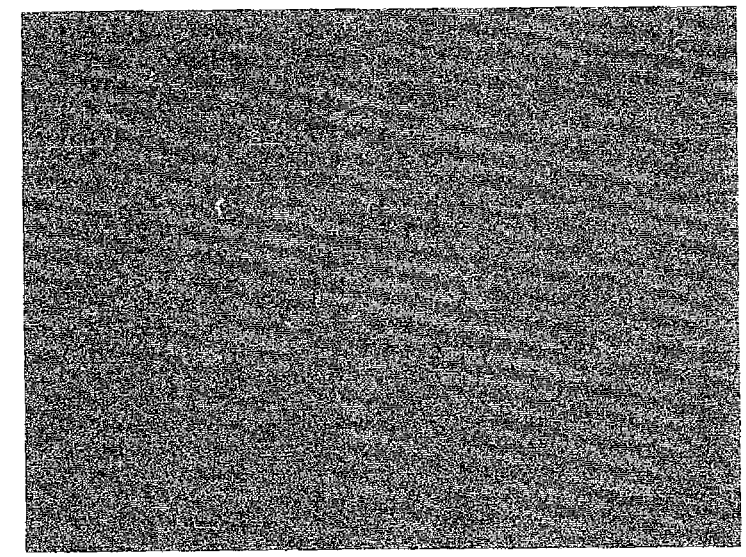

The PGB3 formulation was homogeneous and had very fine and uniform texture as seen under polarized light (FIGS. 3A and 3B). The PGB3 formulation was visually stable and did not separate or discolor throughout the various stability tests and maintained its viscosity at ambient temperature.

The formulation was subjected to Freeze-Thaw-Cycle (FTC), Centrifugation and Accelerated Temperature stability tests, as described hereinabove. The PGB3 formulation was visually stable and did not separate or change its color during all the stability tests. Product viscosity was retained at ambient temperature following the stability tests.

The AS101 formulation did not react with phenol-epoxy internal liner of aluminum tube for 30 days at 40° C., but reacted immediately with the aluminum of the tube opening as soon as the tube was punctured open with the plastic cap and first dispensing, in a non-reversible manner.

An additional exemplary AS101 formulation, containing 15% by weight AS101, was similarly prepared, using a mixture of PEG solvents, PEG 200, PEG 400 and PEG 4000, as described herein, and DMSO. After dissolving AS101 in the mixture of PEG and DMSO, PHOSAL® 50PG and Brij 72 were added. The formulation remained stable upon storage for 3 months days at room temperature.

The following describes additional exemplary formulations according to the present embodiments:

| Component | Weight % | Function |
|---|---|---|
| AS101 | 12.00 | Active ingredient |
| PEG-400 | 39.00 | Solvent/carrier |

-continued

| Component | Weight % | Function |
|---|---|---|
| PEG-200 | 30.00 | Solvent/carrier |
| PEG-4000 | 10.00 | Thickener |
| DMSO | 5.00 | Co-solvent |
| PHOSAL ® 50PG | 2.00 | Skin penetrant |
| Brij 72 | 2.00 | Stabilizer |
| Total | 100.00 | |

| Component | Weight % | Function |
|---|---|---|
| AS101 | 12.00 | Active ingredient |
| PEG-400 | 34.00 | Solvent/carrier |
| PEG-200 | 30.00 | Solvent/carrier |
| PEG-4000 | 10.00 | Thickener |
| Propylene glycol | 5.00 | Co-solvent |
| DMSO | 5.00 | Co-solvent |
| PHOSAL ® 50PG | 2.00 | Skin penetrant |
| Brij 72 | 2.00 | Stabilizer |
| Total | 100.00 | |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A highly stable formulation for topical application, comprising a tellurium-containing compound in an amount of about 12 to about 35 weight percent of the formulation and having at least one tellurium dioxo moiety and a pharmaceutically acceptable carrier, wherein:
said carrier comprises DMSO and at least one polyethylene glycol solvent;
said DMSO is in an amount between about 1% and about 10% by weight of the formulation;
the formulation is chemically and physically stable upon storage at room temperature for at least 30 days; and
said tellurium-containing compound is soluble, dispersible and/or suspendable in said at least one polyethylene glycol solvent at a concentration of about 10 weight percent and
is selected from the group consisting of tellurium dioxide ($TeO_2$), a complex of $TeO_2$, a compound having general Formula I:

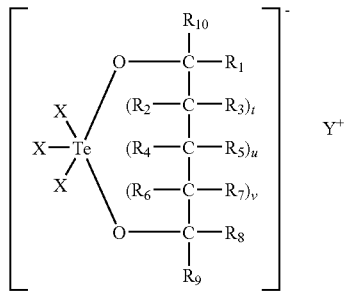

Formula I a compound having general Formula II:

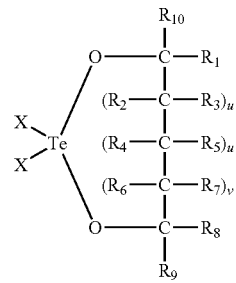

Formula II a compound having general Formula III:

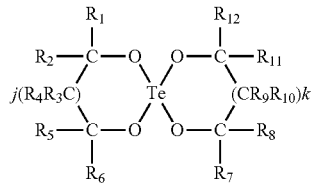

Formula III and
a compound having general Formula IV:

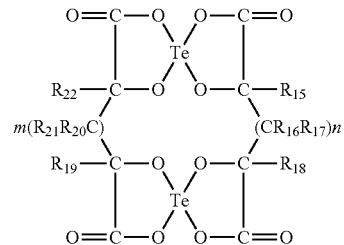

wherein:
each of t, u and v is independently 0 or 1;
each of m and n is independently an integer from 0 to 3;
each of j and k is independently an integer from 0 to 4;
Y is a cation;
X is a halogen atom; and
each of $R_1$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkyl amidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamide.

2. The formulation of claim 1, wherein said carrier is selected such that the formulation is stable upon storage for at least 6 months at room temperature.

3. The formulation of claim 1, wherein said carrier is selected such that the formulation is stable upon storage at 40° C. for at least 30 days.

4. The formulation of claim 1, wherein said carrier is selected such that the formulation is stable upon storage at 40° C. for at least 60 days.

5. The formulation of claim 1, wherein said carrier is selected such that the formulation is stable upon storage at 40° C. for at least 90 days.

6. The formulation of claim 1, wherein said carrier is selected such that the formulation is stable upon cycling at a temperature that alternates at least 3 times from about −10° C. to about 40° C. about every 48 hours.

7. The formulation of claim 1, wherein said carrier is selected such that the formulation is stable upon centrifugation at about 3,000 RPM for 10 minutes and then at 10,000 RPM for additional 10 minutes.

8. The formulation of claim 1, wherein said at least one polyethylene glycol has an average molecular weight that ranges from about 100 Da to about 10000 Da.

9. The formulation of claim 8, wherein said carrier comprises a mixture of polyethylene glycols selected so as to provide the formulation with a desired consistency applicable for topical formulation and/or to provide a formulation that is conveniently applied and/or absorbed.

10. The formulation of claim 1, wherein said carrier further comprises at least one ingredient selected from the group consisting of a stabilizer, a penetration enhancer, a humectant, a deodorant, an aroma modifier, an antiperspirant, a sun screening agent, a sunless tanning agent, a hair conditioning agent, a pH adjusting agent, a sun blocking agent, a chelating agent, a preservative, an emulsifier, an occlusive agent, an emollient, a thickener, a solubilizing agent, an anti-irritant, a colorant, a propellant and a surfactant.

11. The formulation of claim 1, wherein a concentration of DMSO is about 5 weight percent of the formulation.

12. The formulation of claim 1, wherein said carrier further comprises at least one penetration enhancer and said at least one penetration enhancer is selected from the group consisting of propylene glycol (PG), dimethyl formamide (DMF), allantoin, urazole, N,N-dimethylacetamide (DMA), decylmethylsulfoxide ($C_{10}$ MSO), polyethylene glycol monolaurate (PEGML), propylene glycol monolaurate (PGML), Phosal, glycerol monolaurate (GML), lecithin, 1-substituted azacycloheptan-2-ones, alcohols, vegetable oil, phosphatidylcholine concentrate (PC), and mixtures thereof.

13. The formulation of claim 10, wherein said carrier further comprises at least one surfactant.

14. The formulation of claim 13, wherein a concentration of said at least one surfactant ranges from about 1 weight percent to about 10 weight percent.

15. The formulation of claim 13, wherein said at least one surfactant is selected from the group consisting of non-ionic surfactant, anionic surfactant, cationic surfactant and amphiphilic surfactant.

16. The formulation of claim 15, wherein said surfactant is selected from the group consisting of polyoxyethylene sorbitan monolaurate, octoxynol, tyloxapol, nonionic polyoxyethylene surfactants, sorbitan mono-octadecenoate, poloxamers and emulphors.

17. The formulation of claim 1, further comprising an additional active agent.

18. The formulation of claim 17, wherein said additional active agent is selected from the group consisting of an antibiotic agent, an antimicrobial agent, an anti-acne agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, a chemotherapeutic agent, an antidepressant, an antihistamine, a vitamin, a hormone, a keratolytic agent and an antidandruff agent.

19. The formulation of claim 1, wherein a concentration of said tellurium-containing compound ranges from about 15 weight percent to about 20 weight percent.

20. The formulation of claim 1, wherein said tellurium-containing compound has general Formula I.

21. The formulation of claim 20, wherein t, u and v are each 0.

22. The formulation of claim 21, wherein $R_1$, $R_8$, $R_9$ and $R_{10}$ are each hydrogen.

23. The formulation of claim 22, wherein X is chloro.

24. The formulation of claim 23, wherein Y is selected from the group consisting of ammonium, phosphonium, potassium, sodium and lithium.

25. The formulation of claim 1, being a hydrophilic formulation.

26. The formulation of claim 1, being a washable formulation.

27. The formulation of claim 1, having a viscosity in the range of from about 1,000 cpi to about 1,000,000 cpi at room temperature.

28. The formulation of claim 1, having a viscosity in the range of from about 3,000 cpi to about 30,000 cpi at room temperature.

29. The formulation of claim 1, being packaged in a packaging material and identified in print, in or on the packaging material, for use in the treatment of medical condition in which topical application of said tellurium-containing compound is beneficial, wherein said medical condition is selected from the group consisting of scleroderma, psoriasis, atopic dermatitis, scarring, alopecia, hair loss, metastatic melanoma, basal cell carcinoma, actinic keratosis and UV skin damage.

30. The formulation of claim 1, being in a form selected from the group consisting of a cream, an ointment, a paste, a gel, a lotion, a milk, a suspension, a solution, an aerosol, a spray, a foam, a shampoo, a mousse, a serum, a swab, a pledget, a pad, a tincture, a patch and a soap.

31. A method of treating a condition in which topical application of a tellurium-containing compound is beneficial, the method comprising administering to a subject in need thereof a therapeutically effective amount of the formulation of claim 1.

32. The method of claim 31, wherein said condition is selected from the group consisting of scleroderma, psoriasis, atopic dermatitis, scarring, alopecia, hair loss, metastatic melanoma, basal cell carcinoma, actinic keratosis and UV skin damage.

33. A process of preparing the formulation of claim 1, the process comprising mixing said tellurium-containing compound and said carrier.

34. The process of claim 33, wherein said mixing is conducted at a temperature that ranges from about 10° C. to about 100° C.

35. A highly stable formulation for topical application comprising a tellurium-containing compound having at least one tellurium dioxo moiety, the tellurium-containing compound selected from AS101 and SAS, the tellurium-containing compound in an amount of about 10 to about 35 weight percent of the formulation, a carrier comprising DMSO and diethylene glycol monoethyl ether, the carrier selected such that:

said tellurium-containing compound, at a concentration of 10 weight percent, is soluble, dispersible and/or suspendable in the carrier; and the formulation is chemically and physically stable upon storage at room temperature for at least 30 days.

36. The formulation of claim 35, wherein the tellurium-containing compound comprises about 15 weight percent of the formulation.

37. The formulation of claim 36, wherein the tellurium-containing compound is AS101.

38. The formulation of claim 35, further comprising propylene glycol.

39. The formulation of claim 35 further comprising DMSO in an amount by weight percent of at least about 5%.

40. The formulation of claim 39, further comprising propylene glycol.

41. The formulation of claim 1, wherein said tellurium-containing compound is a compound of formula (I).

42. The formulation of claim 1, wherein said tellurium-containing compound is the sole active ingredient in the formulation.

* * * * *